US012558293B2

(12) United States Patent
Hines

(10) Patent No.: US 12,558,293 B2
(45) Date of Patent: Feb. 24, 2026

(54) MEDICATION DISPENSING SYSTEM

(71) Applicant: Dose Health LLC, Golden Valley, MN (US)

(72) Inventor: Paul Hines, Minneapolis, MN (US)

(73) Assignee: Dose Health LLC, Golden Valley, MN (US)

( * ) Notice: Subject to any disclaimer, the term of this patent is extended or adjusted under 35 U.S.C. 154(b) by 0 days.

(21) Appl. No.: 18/666,225

(22) Filed: May 16, 2024

(65) Prior Publication Data

US 2024/0415739 A1     Dec. 19, 2024

Related U.S. Application Data

(63) Continuation of application No. 17/445,355, filed on Aug. 18, 2021, now Pat. No. 12,016,828, which is a
(Continued)

(51) Int. Cl.
*G08B 21/22*          (2006.01)
*A61J 7/00*           (2006.01)
(Continued)

(52) U.S. Cl.
CPC ........... *A61J 7/0445* (2015.05); *A61J 7/0084* (2013.01); *A61J 7/0418* (2015.05); *A61J 7/0436* (2015.05);
(Continued)

(58) Field of Classification Search
USPC ...... 340/573.1, 525, 539.12, 539.13, 539.21, 340/539.22, 539.3, 568.1, 568.8
See application file for complete search history.

(56) References Cited

U.S. PATENT DOCUMENTS 4,572,403 A * 2/1986 Benaroya ................... A61J 7/04
                                                          221/76
6,145,697 A    11/2000 Gudish
(Continued)

FOREIGN PATENT DOCUMENTS

EP        3556341        7/2023
WO      2024263306      12/2024
(Continued)

OTHER PUBLICATIONS

International Preliminary Report on Patentability, International Application No. PCT/US2019/021494, mailed Oct. 20, 2020, 8 pages.

*Primary Examiner* — Daniel Previl
(74) *Attorney, Agent, or Firm* — Merchant & Gould P.C.

(57)          ABSTRACT

A medication dispensing system is provided with several cooperating components which help to accommodate the responsible handling of medications. These systems include a user interface to receive input from the user and to present appropriate information/notices/alarms. Further, physical controls and multiple sensors are provided to detect tampering, misuse, and attempts to inappropriately access medications contained within the dispensing system. This misuse can thus be detected, and appropriate notifications can be provided, where appropriate. Further, by adding network communications capabilities, notices can be widely communicated to others, and operation of the medication dispensing system can be controlled and/or monitored remotely.

18 Claims, 14 Drawing Sheets

Related U.S. Application Data continuation of application No. 16/869,712, filed on May 8, 2020, now Pat. No. 11,116,699, which is a continuation of application No. 16/791,378, filed on Feb. 14, 2020, now abandoned, which is a continuation of application No. 15/707,858, filed on Sep. 18, 2017, now Pat. No. 10,596,072, which is a continuation-in-part of application No. 29/563,171, filed on May 3, 2016, now Pat. No. Des. 806,380.

(60) Provisional application No. 62/396,150, filed on Sep. 17, 2016.

(51) Int. Cl.

| | |
|---|---|
| *A61J 7/04* | (2006.01) |
| *G16H 20/13* | (2018.01) |
| *G16H 40/63* | (2018.01) |
| *G16H 40/67* | (2018.01) |

(52) U.S. Cl.

CPC ............. *A61J 7/0481* (2013.01); *A61J 7/049* (2015.05); *G16H 20/13* (2018.01); *G16H 40/63* (2018.01); *G16H 40/67* (2018.01); *A61J 7/0454* (2015.05); *A61J 2200/30* (2013.01); *A61J 2200/70* (2013.01)

(56) References Cited

U.S. PATENT DOCUMENTS

| | | | |
|---|---|---|---|
| 6,234,343 B1 | 5/2001 | Papp | |
| 6,611,733 B1 | 8/2003 | Huerga | |
| 6,766,219 B1 * | 7/2004 | Hasey | A61J 7/0084 |
| | | | 700/238 |
| 7,044,302 B2 | 5/2006 | Conley | |
| 7,896,192 B2 | 3/2011 | Conley | |
| 8,670,865 B2 | 3/2014 | Coe | |
| 9,278,053 B2 * | 3/2016 | Moore | A61J 7/0427 |
| 9,973,611 B2 | 5/2018 | Pether et al. | |
| 10,022,304 B2 * | 7/2018 | Deeter | A61J 7/0076 |
| 10,265,247 B1 | 4/2019 | Sidi | |
| 10,369,081 B2 | 8/2019 | Hines | |
| 10,596,072 B2 | 3/2020 | Hines | |
| 10,643,451 B2 | 5/2020 | Johnson | |
| 11,116,699 B2 | 9/2021 | Hines | |
| 11,728,021 B2 | 8/2023 | Kamen et al. | |
| 12,016,828 B2 | 6/2024 | Hines | |
| 12,205,697 B2 | 1/2025 | Kamen et al. | |
| 12,223,820 B2 | 2/2025 | Johnson | |
| 2001/0028308 A1 | 10/2001 | De La Huerga | |
| 2002/0088817 A1 * | 7/2002 | Bell-Greenstreet | |
| | | | G07F 17/0092 |
| | | | 221/76 |
| 2003/0127463 A1 | 7/2003 | Varis | |
| 2004/0039481 A1 * | 2/2004 | de la Huerga | A61J 1/1437 |
| | | | 700/236 |
| 2004/0138921 A1 | 7/2004 | Broussard | |
| 2004/0183873 A1 | 9/2004 | Steinmetz | |
| 2006/0230975 A1 * | 10/2006 | Shiwaku | B61B 1/00 |
| | | | 104/88.01 |
| 2009/0152291 A1 | 6/2009 | Ohmura et al. | |
| 2009/0281657 A1 | 11/2009 | Gak | |
| 2010/0121486 A1 | 5/2010 | Yuyama | |
| 2010/0305749 A1 | 12/2010 | Coe | |
| 2013/0018503 A1 * | 1/2013 | Carson | B65D 75/327 |
| | | | 700/216 |
| 2013/0297068 A1 | 11/2013 | Marshall | |
| 2014/0026887 A1 | 1/2014 | Portney | |
| 2014/0090644 A1 | 4/2014 | Aldana | |
| 2014/0278510 A1 * | 9/2014 | McLean | G16H 20/13 |
| | | | 705/2 |
| 2016/0227736 A1 * | 8/2016 | Monk | A01K 5/0142 |
| 2017/0000693 A1 | 1/2017 | Orr et al. | |
| 2017/0021950 A1 | 1/2017 | Bouthiette | |
| 2017/0326033 A1 | 11/2017 | Kraft | |
| 2017/0348194 A1 | 12/2017 | Duda | |
| 2017/0354574 A1 | 12/2017 | Feng | |
| 2018/0064608 A1 | 3/2018 | Hines | |
| 2023/0343158 A1 | 10/2023 | Poddar | |
| 2023/0343159 A1 | 10/2023 | Poddar | |
| 2023/0351827 A1 | 11/2023 | Poddar | |
| 2023/0360454 A1 | 11/2023 | Poddar | |
| 2023/0360455 A1 | 11/2023 | Poddar | |
| 2024/0265756 A1 | 8/2024 | Poddar | |

FOREIGN PATENT DOCUMENTS

| | | |
|---|---|---|
| WO | 2024263307 | 12/2024 |
| WO | 2024263308 | 12/2024 |

* cited by examiner

MEDICATION DISPENSING SYSTEM

CROSS REFERENCE TO RELATED APPLICATIONS

This application is a continuation of U.S. patent application Ser. No. 17/445,355, filed Aug. 18, 2021, now issued as U.S. Pat. No. 12,016,828, which is a continuation of U.S. patent application Ser. No. 16/869,712 filed May 8, 2020, now issued as U.S. Pat. No. 11,116,699, which is a continuation of U.S. patent application Ser. No. 16/791,378 filed Feb. 14, 2020, which is a continuation of U.S. patent application Ser. No. 15/707,858 filed Sep. 18, 2017, now issued as U.S. Pat. No. 10,596,072, which claims the benefit of U.S. Provisional App. Ser. No. 62/396,150, filed Sep. 17, 2016, and is further a continuation in part of U.S. patent application Ser. No. 29/563,171, filed May 3, 2016, now issued as U.S. Design Patent No. D806,380, the contents of the aforementioned applications being hereby incorporated by reference in their entirety. This application is further related to U.S. patent application Ser. No. 15/707,996, now issued as U.S. Pat. No. 10,369,081, the contents of which are hereby incorporated by reference in their entirety.

BACKGROUND

The present invention is in the technical field of consumer medical medication dispensers and related systems. More particularly, the present invention is in the technical field of medication dispenser systems with improved efficiency and safety features.

The proper handling of medication is a significant concern in today's society. Clearly, the use of medication in various medical treatments will help individuals enjoy an improved quality of life, and has contributed to increased life expectancies. Misuse of drugs can created severe consequences, including death from overdose.

Medication dispensers often have issues or complications with both security and usability. In addition, very few extend their feature set to be enabled to store timing of events and allow that data to be transferred to the internet or remote server. Additional security features to prevent tampering of medications, undesired access and misues are a welcome addition to any pillbox.

Medication dispensers can be connected to remote servers allowing data (e.g. time when taken, missed medications, relevant statistics) and notifications (e.g. text, emails, phone calls) to be sent to interested parties (e.g. family caregivers, home health care, hospitals, insurance agencies, pharmacies, pharmacy benefit managers). However ownership and the privacy of this data has not been addressed adequately in the prior art. In addition, laws like HIPAA specify certain restrictions in how protected health information (PHI) is sent to covered entities. User interfaces are also difficult to navigate with current medication dispensers and a robust model of replaceable cassettes has yet to be implemented.

SUMMARY

The present medication dispenser and related systems provide a set of features that increase the security and the usability of a medication dispenser.

In addition, a method is provided to ensure that proper ownership is maintained for the data and notifications of a medication dispenser while still enabling that data to be shared in a secure and repeatable manner. A user interface to better associated dispense times, medications, and compartments in a cassette is described. A generic and custom labelling system associated with a medication dispenser is described, along with several some cassette specific features.

BRIEF DESCRIPTION OF THE DRAWINGS

Further objects and advantages of the medication dispenser can be seen from reading the following detailed description, in conjunction with the drawings in which:

FIG. 9 illustrates a further user interface for medications and their associated dispense times;

FIG. 10 shows a further specified user interface;

FIG. 11 shows a corresponding subsection of the user interface;

Figure 12:
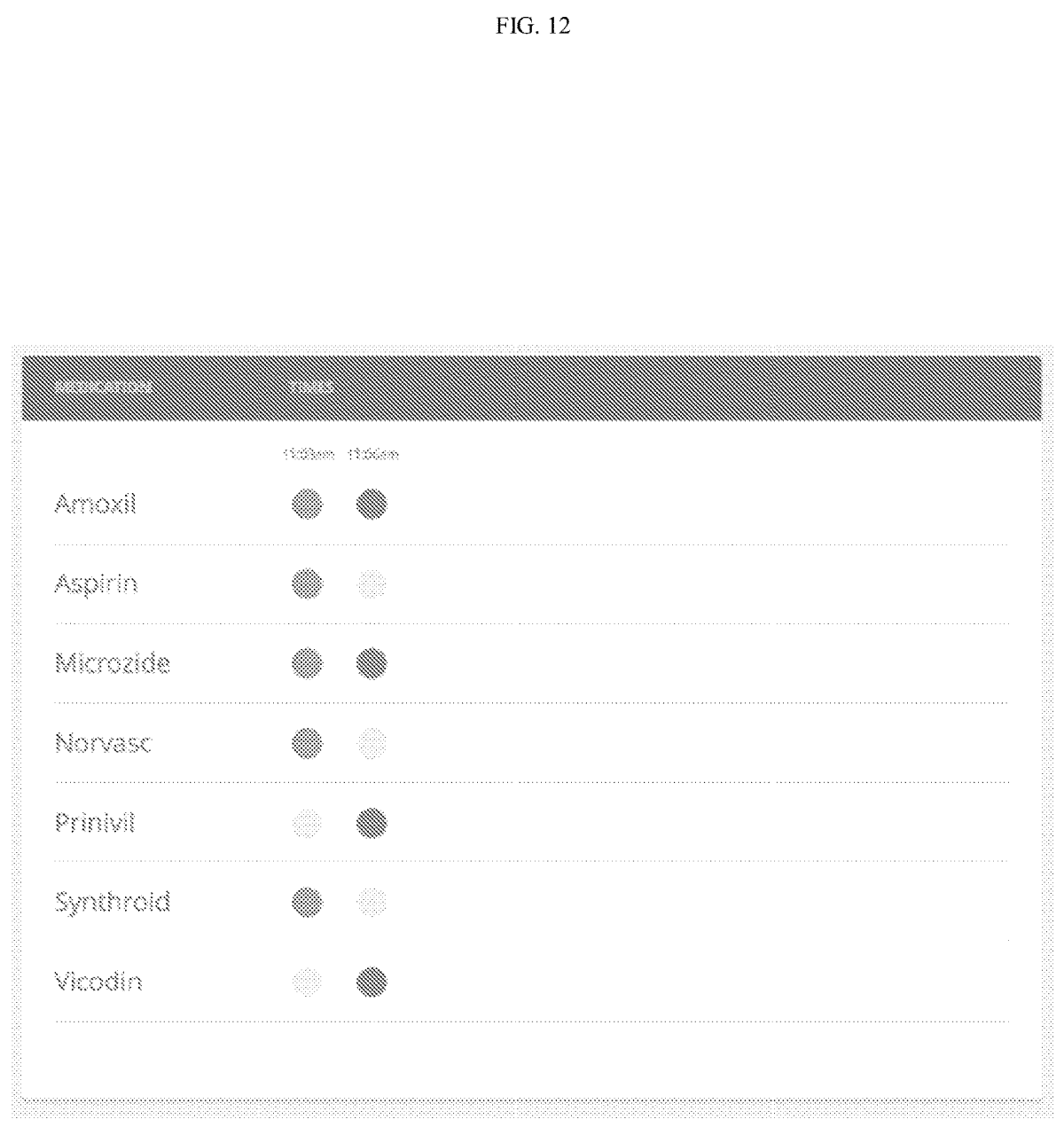

FIG. 12 is yet a further illustration of a user interface for medications and their associated dispense times;

DESCRIPTION

Figure 1:
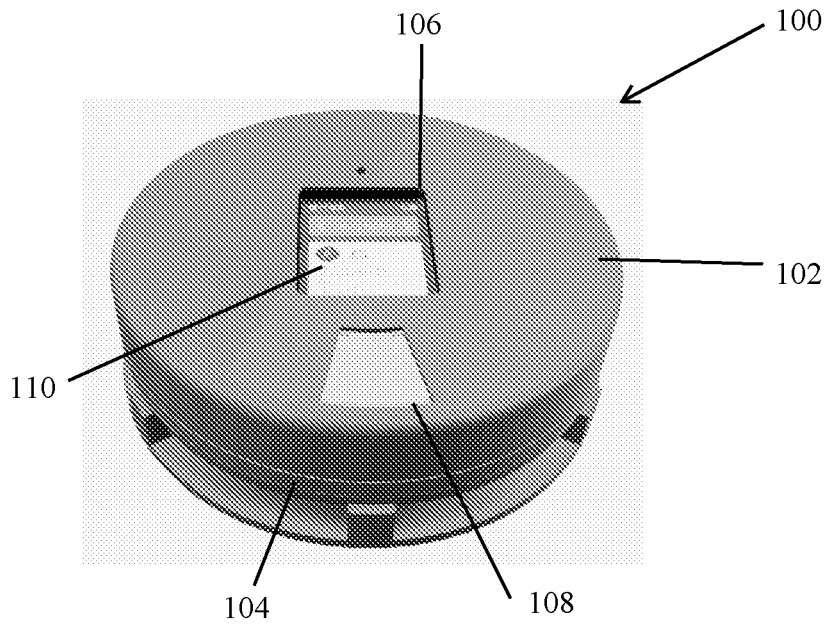
FIG. 1 is a perspective view of a medication dispenser.

In an effort to accommodate the proper handling of medications and drugs, a medication dispenser 100 incorporates several safety features, including physical structures and systems to produce warning signals, notices, and lockouts. All of these features combine to produce a medication dispenser 100 that more effectively controls the responsible handling of drugs and medications.

FIGS. 1-4 illustrate medication dispenser 100, which includes a cover 102 mounted to a base 104. Cover or lid 102 includes a first aperture 106 and a second aperture 108. Aligned with the first aperture 106 is a display screen 110, while the second aperture is aligned with a cassette 112. The cassette 112 includes a plurality of compartments 114A-N as well as a covered compartment 116. Cassette 112 rotates about a central axis as operated through a control assembly 118 and a drive member 120. In one embodiment, the cassette 112 interfaces with the drive member 120 to rotate therewith about the central axis. A port 122 is provided in the base 104 that is in electrical communication with the control assembly 118 so as to provide power thereto. Port 122 may also provide an interface to related systems. In one example, port 122 may be a USB port.

The control assembly 118 is operatively coupled with the display screen 110 and drive member 120. The display screen 110, in one embodiment, is a touch screen that receives input from a user and displays information related to loading and operation of medication dispenser 100. The drive member 120 is coupled with a motor (not shown) of the control assembly 118 to rotate about the central axis. During operation, as directed by the control assembly 118, the drive member 120 rotates cassette 112 about the central axis in order to align one of the plurality of compartments 114 with aperture 108.

To that end, the cassette 112 includes a plurality of discrete positions about the central axis. In the illustrated embodiment, the cassette 112 includes 15 discrete positions about the central axis, one for each compartment and one for the covered compartment.

In one embodiment, the cassette 112 includes a home or reference position relative to the display screen 110. Accordingly, the display screen 110 is configured to display information about each of the plurality of compartments 114, including an identifier for each compartment in immediate proximity to the compartment. During loading of the dispenser 100, the identifier for each compartment can be highlighted or otherwise provide an indication of medication to be positioned within the adjacent compartment.

As further outlined below, medication dispenser 100 includes several unique features which provide unique capabilities. It is understood that the present embodiment will include each of these features, but variations may exists, including omitting certain features.

Touchscreen Interface:

Typically, pillboxes or medical dispensers do not have an interactive display, or much of a user interface. That said, display screen 110 (also referred to as touchscreen 110) provides medication dispenser 100 with several additional features and capabilities. As one example, a passcode interface could be utilized which only allows access to certain menu items when the correct combination is entered. It should be noted that many types of user interfaces could be used, including physical buttons, electronic sensors, and related displays. The passcode could also be used so that only the correct person (i.e. a home health aid) would be allowed to have medication dispenser 100 dispense medications at a certain time. The status of medication dispenser 100, including what medications are loaded, and the location of such medications, could also be displayed on the touchscreen 110. Further, WiFi or other connection setup could also be accomplished through touchscreen 110.

Additional features are also enabled by having touchscreen 110 included as part of medication dispenser 100. This could include tracking personal care attendants for home health care, tracking each of their duties, or logging work hours. With the openness of a touchscreen based platform, any number of events could be track and could be classified as "touchscreen" events. The timing and history of these event can be recorded in digital memory in medication dispenser 100, and with an internet connection to a remote server, the event and time can be stored in a remote database. Connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on touchscreen 110 or other similar interfaces.

Figure 2:
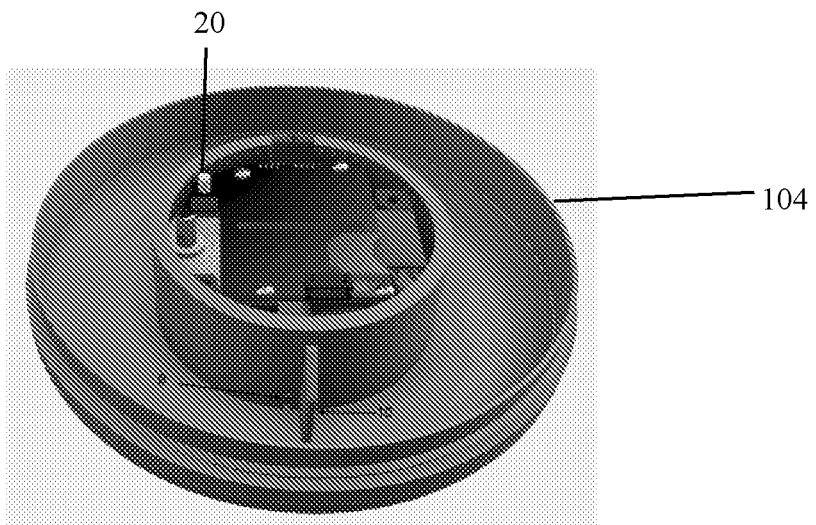
FIG. 2 is a perspective view of the medication dispenser of FIG. 1 with portions removed to illustrate a control assembly and drive member.
Figure 3:
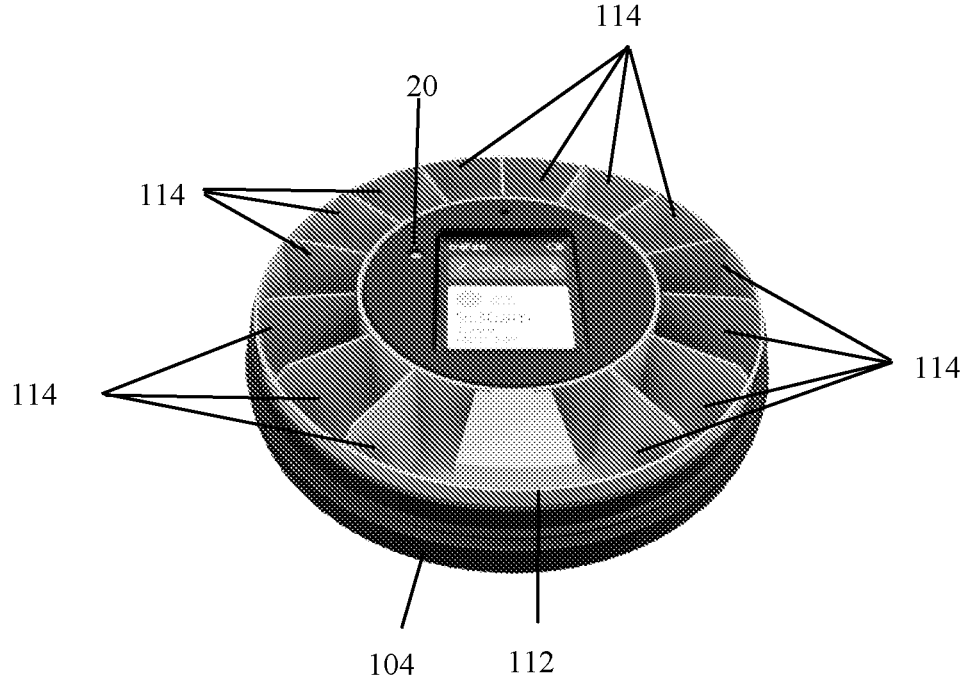
FIG. 3 is a perspective view of the medication dispenser of FIG. 1 with portions removed to illustrate a cassette.
Figure 4:
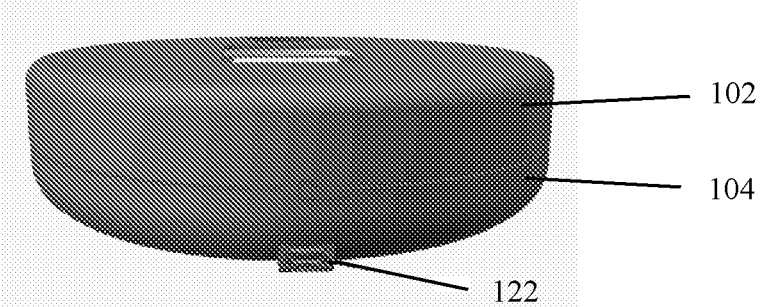
FIG. 4 is a rear perspective view of the medication dispenser of FIG. 1.

Opening Switch:

As generally illustrated in FIGS. 2 and 3, an additional level of security is provided by including an opening switch

20, which is positioned in such a way to recognize when cover or lid 102 of medication dispenser 100 is opened or removed from the base 104. Opening switch 20 could be either mechanical, as in this embodiment, or could be any alternative sensing medication dispenser 100s, such as proximity sensors, light intensity sensors or laser gating mechanisms. A knob or similar structure on the underside of the lid 102 (not shown) could also facilitate the mechanical motion of the opening switch 20 when closing the lid 102.

When the lid 102 is opened or separated from the base (or, the reverse, securing onto the base), the opening switch 20 is activated. The changing of the status of the opening switch 20 can activate an "opening" or "closing" event. The timing and history of these event can be recorded in control assembly 118 within medication dispenser 100. As further discussed below, control assembly will include several components, including memory, a processor or microcontroller, and related interface components. One such interface component will provide an internet connection to a remote server (which allows the event and time to be stored in a remote database). Connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on medication dispenser 100 through touchscreen 110.

Opening switch 20, in conjunction with the associated data recording and notifications, can be used to enhance the security of medication dispenser 100 as unexpected events would be an indication that someone may be tampering with medication dispenser 100. In addition, opening switch 20 could lead to prompting of events on medication dispenser 100 through touchscreen 110, as further discussed below. For example, once the lid 102 is removed ("opened"), opening switch 20 could trigger a touchscreen 110 interface to automatically prepare medication dispenser 100 for refilling (i.e. medication dispenser 100's cassette rotates into the proper location). If medication dispenser 100 is not being tampered with, then the lid 102 would likely only be removed when medication dispenser 100 is prepared for a refill (as in the current embodiment). Further, an alarm could also sound if the opening was not at an expected time.

Cassette Switch:

A cassette switch 30 is positioned in base 104 in such a way to sense when the cassette 112 is removed from or placed in medication dispenser 100. Cassette switch 300 could be either mechanical, or could function in other manners such as measuring light intensity or laser gating. When the cassette is removed or placed, the cassette switch 30 is activated and is able to trigger a "cassette change" event.

The timing and history of these cassette change events can be recorded in control assembly 118 within medication dispenser 100. Again, with an internet connection to a remote server, any cassette related events and related times can be stored in a remote database. Connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on touchscreen 110.

Cassette switch 30, along with all associated recordings and notifications, can be used to enhance the security of medication dispenser 100 as it would be an indication that someone may be tampering with medication dispenser 100 (if the event was unexpected). In addition, cassette switch 30 could lead to prompting of events on medication dispenser 100 through an interface such as a touchscreen 110 (see below). For example, once the cassette is removed then cassette switch 30 could trigger a touchscreen 110 interface to automatically prepare medication dispenser 100 for refilling. If medication dispenser 100 is not being tampered with, then the cassette would likely only be removed when medication dispenser 100 is ready for a refill (as in the current embodiment). An alarm could also sound if the cassette removing or adding was not at an expected time.

Figure 5:
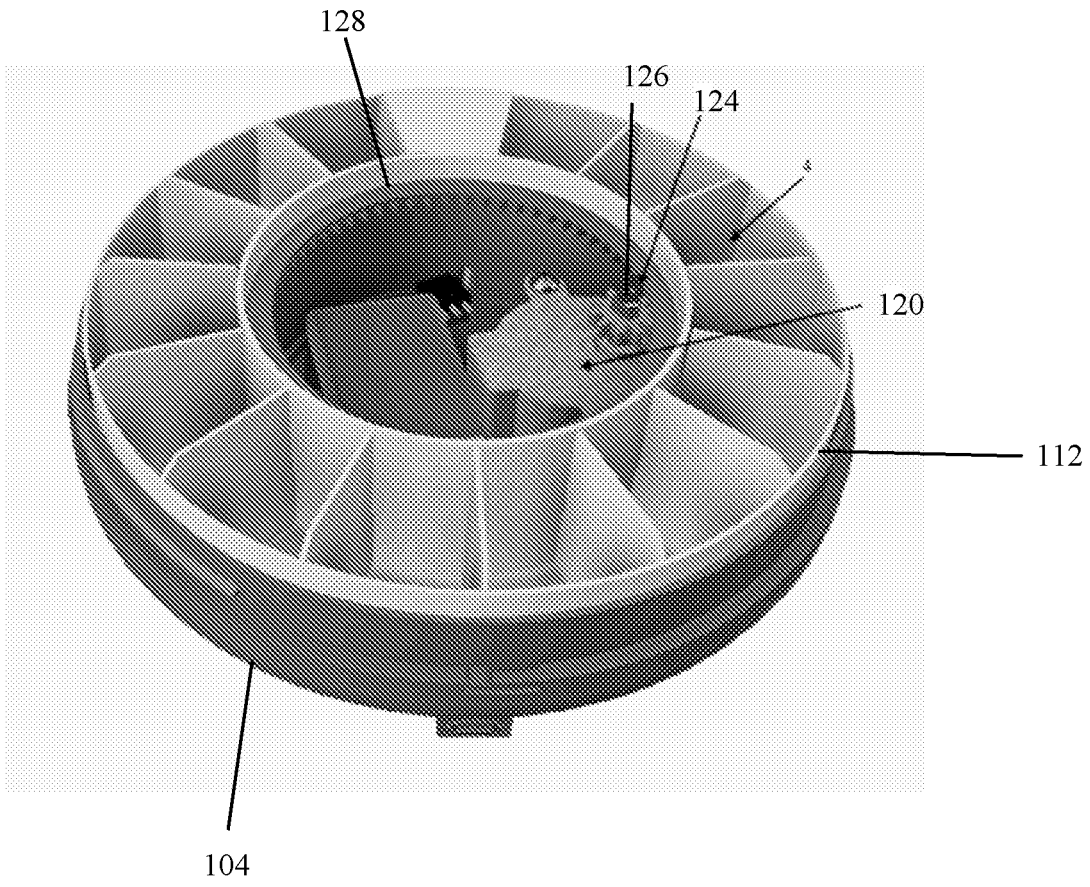
FIG. 5 illustrates a partial assembly view, with the lid 102 and a control/display panel removed.

Manually Motor Detection for Cassette Tampering:

As mentioned above, and better illustrated in FIG. 5, a drive member or motor 120 is used to drive cassette 112 in a circular motion. Motor 120 can also be used to detect when medication dispenser 100 is misaligned or has been tampered with. With the current embodiment, a user could use their fingers or some other tool to manually move the cassette so that adjacent compartments could be accessed (through the lid 102 aperture for example). The user could then take medications outside of their prescribed times if either of these or other compartments contained medications. Although it may take considerable force to manually move the cassette, it is valuable to know if it has been moved intentional or unintentionally, to insure proper alignment of the compartments with the lid 102 aperture or as evidence of tampering. Cassette 112 is coupled to motor 120 through a guide piece and gear mechanism 124. When cassette 112 is turned manually (not through the action of the motor) then the gear mechanism 124 and drive shaft 126 of motor 120 will also spin. This spinning of the motor drive shaft 126 will generate an electrical signal that can be recognized by the control assembly 118 of medications medication dispenser 100 as a specific "motor spin" event. The timing and history of these event can be recorded in digital memory of control assembly 118, and/or in a remote database (via appropriate internet connection). Connection to the internet also allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on touchscreen 110.

Accelerometer:

To provide further control of medications, an accelerometer 40 is positioned within medication dispenser 100. Primarily, accelerometer 40 can be used as a mechanism to determine if someone has flipped medication dispenser 100 during the interval when medication are available. This would trigger a "taken" or "dispensed" event and associated actions could be taken. More specifically, this indicates that a user has "dumped" medication from the open compartment.

Accelerometer 40 could also be used to determine the orientation of medication dispenser 100 to ensure it is being used correctly. In the current embodiment, medication dispenser 100 should initially be placed with the aperture facing upwards to ensure that medications are appropriately position for delivery. Medication dispenser 100 then needs to be flipped to access the medications (and that this motion can be recorded). If someone were to place medication dispenser 100 on a table with the aperture downwards (i.e. face down), this improper orientation could be recognized by the accelerometer 40 and trigger a "orientation off" event. The same event could also trigger if medication dispenser 100 was placed in a purse or backpack because is unlikely that medication dispenser 100 would be in the upright orientation. If medication dispenser 100's orientation is not upright based on the accelerometer 40 reading, then medication dispenser 100 could be prevented from moving to the next compartment with medications, until it is in the proper position. A buzzer or other action as specified below could also be triggered when medication dispenser 100 was in the incorrect orientation.

The accelerometer 40 could also recognize if there was any motion that would be consistent with a fall of medication dispenser 100, i.e. there would be a threshold of acceleration. Calculated g-forces would then indicate that the event was likely not an "orientation off" but a "fall" event. In the senior population, this would be particularly valuable as they are less likely to have the dexterity to hold onto medication dispenser 100 and medication dispenser 100 drops would be more frequent. When a "fall" event occurred, the user or caregiver of medication dispenser 100 could be notified as specified below, the buzzer within medication dispenser 100 could also be set to trigger. Once a fall occurred and was tracked by the accelerometer 40, a user could follow up immediately to see any damage was done to medication dispenser 100.

The accelerometer 40 could also be used as a means to control medication dispenser 100 without a conventional mechanical switch 20 or other more involved interfaces such as a touchscreen 110. Light touches could trigger, "tap" events on medication dispenser 100 and different areas could be recognized by the accelerometer 40 (based on how the orientation of medication dispenser 100 is changed) and be associated with control of the settings on medication dispenser 100 (cycling through menus for example).

The accelerometer 40 could also be used to "wake" medication dispenser 100 from a low power or sleep mode as motion would indicate that someone was likely interacting with medication dispenser 100.

There are any number of events that can be tracked by accelerometer 40. It is possible to have real-time tracking rather than triggering of specific events. The events described above ("taken", "dispensed", "orientation off", "fall", "tap") are just some of the examples. For these events and other possible events, including real-time tracking—the timing and history of these event can be recorded in digital memory in medication dispenser 100, and with an internet connection to a remote server, the event and time can be stored in a remote database. Connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on medication dispenser 100 through touchscreen 110.

Actuator or Screw Locking:

In order to provide further tamper resistance, a combination of physical structures are used to prevent easy access to the interior of medication dispenser 100. One such structure or mechanism is a less common screw, such as a torx head screw, and the associated wrench is used to prevent medication dispenser 100 from opening (i.e. "locking" the dispenser). The locking of medication dispenser 100 will help to prevent unintended access to medications for parties that are not the intended users (i.e. children) or undesired desire access to medications outside of the prescribed schedule. The specialized screw spans the lid 102 of medication dispenser 100 and attaches to base 104 of medication dispenser 100. Having a screw keeping the lid 102 and the base connected, prevents them from being separated and exposing the medications without first removing the screw. In order to remove the screw, a wrench with the proper shape must be used. Using a less common screw type, e.g. torx, makes it less likely that the typical user would be able to open medication dispenser 100 (i.e. it is locked).

Rather than having a screw and wrench combination to lock medication dispenser 100, an actuator could be placed within medication dispenser 100 to serve as the lock. A piston within the actuator could secure the lid 102 to the base 104. The mechanism to accomplish locking the lid 102 to the base is unique in the current embodiment. Because the lid 102 is attached to the base with a screw thread spanning the inner edge of the lid 102 and outer edge of the base (FIG. 6), an actuator based locking mechanism would only need to send the piston through the both the lid 102 and base 104. A piston spanning both these parts, would prevent them from rotating with respect to one another. This would thus prevent the lid 102 from unscrewing from the base and would lock medication dispenser 100 closed. This would be more difficult to accomplish with a hinge based mechanism attaching the lid 102 and the base together, as the action of the piston will more likely be parallel to the action of the hinge and thus opening the lid 102 would allow the piston to thread through the hole (in the lid 102) that prevent opening with a screw based mechanism.

An advantage of an electric actuator is that it can be controlled remotely or locally through a touchscreen 110 interface. With medication dispenser 100 having a connection to a remote internet server, the actuator could be controlled by a secure user interface on a web page (or other means, e.g. text messages). This could be a caregiver or a healthcare worker that is responsible for a patient. It would be possible to have medication dispenser 100 only unlocked through a web interface if desired. Additionally, the actuator could be controlled by a touchscreen 110 or other interface on medication dispenser 100. This method would allow someone to be forced to enter a passcode or other security measure on medication dispenser 100 to lock or unlock it.

The positioning of the on and off switch 20 for medication dispenser 100 with respect to the lid 102 and locking mechanism is also an advantage of the current embodiment (not shown). If the on and off switch 20 is positioned in such a way that it is only accessible if the lid 102 is "unlocked" and removed (i.e. underneath the lid 102), this would prevent a user from quickly turning off a medication dispenser 100 (if simultaneously connected to backup battery power).

Alignment Switch:

In the current embodiment, in order to make a compartment containing medications available to the user (i.e. aligned with aperture 108), the cassette 112 containing the compartments and the corresponding medications should be moved into the correct position with respect to aperture 108. As the motor 120 continues to function, there is often some slight variability with the alignment of the cassette 112 with the lid aperture 108. Over the course of continual use, these alignment errors may aggregate causing the alignment of the cassette to become incorrect. This could make it more difficult to have the correct compartment accessible at the right time to dispense the correct medications.

To offset this difficulty, an alignment switch 50, which can be mechanical or otherwise (i.e. light intensity), is placed in medication dispenser 100 to realign the cassette with respect to the aperture 106 (and medication dispenser 100 as a whole). In the current embodiment, alignment switch 50 is located on the inside of a ring 128 that is powered by motor 120 and that the cassette fits onto. When ring 128 and hence cassette 112 is rotated by the motor 120, the alignment switch 20 (attached to the base but facing the inner face of the ring 128) is positioned in such a way to track the motion of the rotating cassette. During certain alignments of cassette 112 with respect to base 104, alignment switch 50 is triggered. This would cause an "alignment" event. The "alignment" event could then cause the motor to adjust the alignment of the cassette with respect to the base and aperture (i.e. realign the cassette) or trigger other actions as specified below. This could also be used as a measure of tampering. If alignment of cassette 112 is significantly out of place, it could indicate someone was manually moving the cassette and tampering with medication dispenser 100. Touchscreen 110 or other interface in conjunction with the alignment switch 50 could allow someone to have medication dispenser 100 perform one full rotation of the cassette 112 (as in the current embodiment) to have the alignment switch 50 trigger and ensure that alignment was proper. This could also occur when medication dispenser 100 is restarted after losing power, since it is more likely that the alignment would then be off (and without power, changes in cassette orientation by manually manipulation could not be sensed by motor detection as specified above).

In the current embodiment, there is a notch on the inner face of ring 128 that is used for realignment as specified above. Rather than having one notch that triggers the alignment switch 20, there could be several notches along the inner face of ring 128 indicating different positions. As alignment switch 50 is mechanical or otherwise, the resulting signal is binary, either on or off. With a binary signal, it is not possible to determine between one notch triggering the alignment switch 50 from a separate notch triggering the alignment switch 50 because both give the same binary signal. To overcome this difficulty, several notches (or other triggering means) could be put in patterns that are triggered in certain time frames. For example, if two notches are adjacent to one another, then they could subsequently be triggered within a small time frame based on the speed of the cassette rotation. Two triggers in a specified time frame could indicate a particular alignment, whereas only one trigger in a specified time frame could indicated a separate alignment (e.g. cassette at 180 degrees vs. 360 degrees). These could all be separated into "alignment" events.

The timing and history of these event can be recorded in digital memory in medication dispenser 100, and/or the event and time can be stored in a remote database. Again, connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on medication dispenser 100 through an interface like a touchscreen 110.

Unplugging Monitor:

In an effort to provide more information regarding the operation and maintenance of medication dispenser 100, monitoring electrical power characteristics can be beneficial. By determining voltage levels supplied to control assembly 118 (i.e. the electronics controlling medication dispenser 100) it is possible to determine if medication dispenser 100 is plugged into wall power or if it running off battery power. This is an advantage to medication dispenser 100, as it allows for prompts to be provided to the user for particular settings automatically, especially when going into battery mode from wall power. One of these modes could be a travel mode. Once medication dispenser 100 was unplugged, medication dispenser 100 could ask the user if it would like to go into travel mode (touchscreen 110 can provide the necessary user interface to carry out this inquiry). Travel mode could consist of medication dispenser 100 being prevented from automatically moving the cassette to the next compartment, but instead requiring a user to enter a passcode or press a button. Other alarms (i.e. orientation triggered) could also be removed in travel mode. Travel mode would also be advantageous if a medication dispenser 100 is carried in luggage or in a purse and the orientation would be variable (e.g. flipped in a purse). Unplugging at unexpected times could also indicate that medication dispenser 100 is possibly being tampered with.

When medication dispenser 100 is unplugged (or plugged in) and this is recognized by control assembly 118 within medication dispenser 100, this is identified as an "unplugged" or "plugged" event. The timing and history of these events can be recorded in digital memory within control assembly 118. Again, with an internet connection to a remote server, the event and time can be stored in a remote database. Connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on touchscreen 110.

Charging Base:

Various charging and power supply options can be provided to medication dispenser 100. Rather than using a typical female and male jack, medication dispenser 100 could use induction (or contact pins) charging to charge the battery. This option makes it possible to quickly remove medication dispenser 100 from a charging station without having to unplug medication dispenser 100. Similarly, medication dispenser 100 could then it could be placed on the charging base to quickly begin charging when needed. Similar to the unplugging monitor discussed above, all of the same features would be available to the charging base with regard to monitoring the placement on the base (i.e. identifying as an "unplugging" and "plugging" event). The timing and history of these event can be recorded in digital memory in control assembly 118, and with an internet connection to a remote server, the event and time can be stored in a remote database. Connection to the internet allows notifications to be sent to any number of people or interested organizations or people about this specific event, where these notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on medication dispenser 100 through touchscreen 110.

Wifi Connection Monitoring:

Medication dispenser 100 in the current embodiment maintains an active internet connection by default. While this could be WiFi, or a cellular connection, tt is advantageous to know the status of this connection. If medication dispenser 100 is moved to a new area without internet connection (i.e. out of wifi or cellular range) it could trigger a travel mode prompt as specified above. Losing internet connection could indicate medication dispenser 100 is being tampered with as well (electronics destroyed for example). The loss of an existing internet connection, or the gain of a new connection, could be considered a "connected" or "disconnected" event. The timing and history of these event can be recorded in digital memory in control assembly. Once again, with an internet connection to a remote server, the event and time can be stored in a remote database. Connection to the internet allows notifications to be sent to any number of people or interested organizations or people about this specific event. These notifications can be in any form such as text (SMS) messages, phone calls, or other means, such as dashboard reports. The recording of these events could be used to identify patterns and help stop tampering or help customers use medication dispenser 100 correctly. If medication dispenser 100 is not connected to the internet, then the recording of the event could be stored in local memory and transferred at a later time or displayed locally on touchscreen 110.

Storing Status of each Compartment:

Similar medication dispensers configured in a circular or other arrangement typically do not store real time information about the status of each of the compartment holding the medications. That said, storing information regarding the status of each compartment (i.e. pills dispensed, pills missed, pills skipped), combined with a circular nature of medication dispenser 100, allows for additional feature that are not present in other products. If a medication is not taken in a desired time frame, then the circular cassette can rotate backwards to the last compartment that was empty and hence help prevent double dosing (because the above mentioned status information is stored in digital memory). If the user continues to skip medications, medication dispenser 100 could continue to return to an empty compartment, and then back to a filled compartment and back to an empty compartment and so on. This would reduce the number of refills as every missed dose would be presented repeatedly through the aperture until it is taken.

Another option is that the circular cassette always moves forward regardless if a medication is taken or not. At the end of the compartments on the circular cassette, the cassette could loop back around and attempt to dispense any missed medications if they are the correct medications for that time of day. These two different options could be selected for with an interface on medication dispenser 100 or through a web portal.

Calendar Syncing:

With active schedules, users of medication dispenser 100 may have varying times and places they take their medications depending on the day of the week (or month). For example, a user may always take medications at 10:00 am on Saturdays when out for breakfast, rather than the typical Monday through Friday 8:00 am schedule. These more complex schedules could be programmed in advance, either through a web interface or on touchscreen 110 on medication dispenser 100. A remote server could be responsible for sending the updated schedule when the day of the week arrives. If someone were to use a service like Google Calendar, this could automatically be uploaded on to medication dispenser 100 based on events on that calendar.

Figure 6:
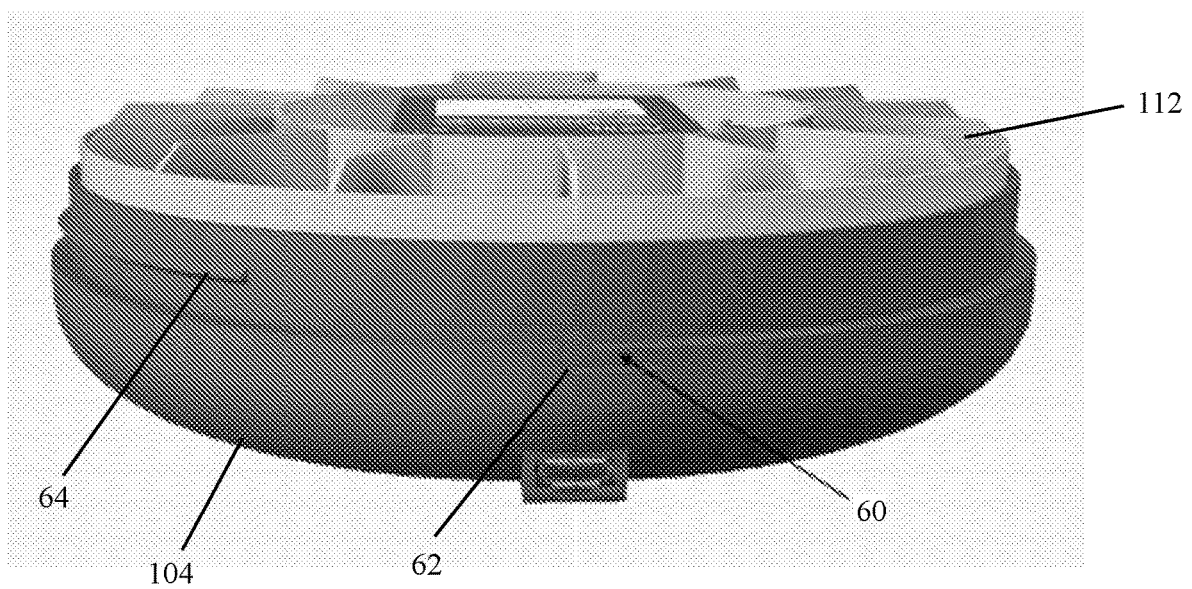
FIG. 6 is a further partial assembly view showing a front side of the medication dispenser.

Screw Lid:

The prior art is limited in the number of pillboxes that use a screw mechanism to secure a lid 102 over medication dispenser 100. In the current embodiment, a screw lid is used for a more streamlined design, more reliable performance, and easier manufacturing. As illustrated in FIG. 6, to secure screw lid 102 at the end point, a simple notch can be used to provide additional force to position the screw lid 102 at the correct location. The screw mechanism of lid 102 and base 104 provides this screw-in coupling 64. To provide locking, a spring loaded tab 60 is provided, and which cooperates with a notch 62. To open lid 102 by the screwing motion, the spring lock must first be released with a downward motion at the lever. This could be used to prevent unnecessary tampering and to prevent children or other parties from easily opening medication dispenser 100.

Integrated USB Wall Charger and WiFi Hotspot:

Many seniors who would most benefit from a medication dispenser 100 do not have WiFi enabled networking in their homes. If a WiFi module is used as in the current embodiment, then the potential user would not have access to the multiple features associated with this connection. To enable medication dispenser 100 to have access to the internet in these circumstances, medication dispenser 100 could have an embedded or separate cellular connection. A cellular connection could be maintained in a medication dispenser 100 with a WiFi module through a separate WiFi hotspot. However, having a separate WiFi hotspot is a disadvantage to the user while traveling, or otherwise, because they would have to remember more than one medication dispenser 100 to enable internet connectivity. To offset this problem, a medication dispenser 100 could be made that integrates a WiFi module with a cellular module (and thus be a WiFi hotspot) with the USB Wall Charger that is already paired with medication dispenser 100. To allow charging with the current embodiment, a USB Wall Charger is used to transfer the power from a wall socket to a USB cord and then to medication dispenser 100 (as commonly done with many cellular phones). When travelling, the charging cord and USB Wall Charger are commonly taken with medication dispenser 100. If the USB Wall charger also had the electronics necessary to power a WiFi hotspot within its housing, it would allow the user less items for which to keep track. The WiFi hotspot would not need its own separate USB Wall Charger (and associated USB cord) for power and instead could draw power from the same medication dispenser 100 that powers medication dispenser 100. In sum, for a user with less access to WiFi, in the current embodiment they would need medication dispenser 100, an integrated USB Wall Charger and WiFi hotspot (all within one housing) and associated USB cord for the complete package versus a medication dispenser 100, a USB Wall charger for medication dispenser 100, a USB cord for medication dispenser 100, a USB Wall Charger for the WiFi hotspot, and a USB cord for the WiFi hotspot (2 less items).

Owner Account Setup and Use:

To perform the various features outlined above, the system must be configured appropriate. This will insure that data is responsibly maintained, and any data sharing is achieved in a responsible manner. This initially involves setting up the owner account, which involves the following:

1. When medication dispenser 100 is first received, the user can be instructed how to connect medication dispenser 100 to a remote internet server through a method like a smartphone app or computer terminal. The connection could be through WiFi, cellular, or any other connection type.

2. Once connected, the dispenser could indicate that a web page or app should be reached by the user in order to create an "owner" account with medication dispenser 100.

a. The internet connection setup of step 1 could be completed after "owner" account registration of steps 2-5. The user may prefer to have the entire setup ready prior to bringing medication dispenser 100 to the pill-taker's place of residence (who may not be the "owner") where the internet connection must be maintained (unless it is cellular) and therefore, steps 2-5 could be completed before step 1.

3. After the user reaches the web page or app and completes a standard account registration process (i.e. fields such as name, email, password), she can be asked for the serial number of medication dispenser 100 which is its unique identifier distinguishing it from other medication dispenser 100s. She could also choose to be a subscriber rather than an owner (as specified below) and not have to enter a unique serial number.

a. The serial number could be labelled on medication dispenser 100 or could be maintained in digital memory and accessed through a screen interface (e.g. an LCD touchscreen 110)

4. The user would then enter the serial number of medication dispenser 100 into the web page or app to begin associating a medication dispenser 100 with a user account that was setup in step 3.

5. The remote server would then send a signal to medication dispenser 100 to place it into a mode that would require the user to interact physically with medication dispenser 100 to finish registration and pair medication dispenser 100 with the user account. This could be a press of a touch screen with associated message or some other action that could only be completed on medication dispenser 100 such as a physical button press. Having the user perform an action on medication dispenser 100 to finish pairing an owner account with medication dispenser 100, prevents users who do not own a particular medication dispenser 100 from claiming that medication dispenser 100 remotely. This would serve to enhance security and could be optional if too burdensome on the user.

6. The user could then interact with medication dispenser 100 through a touchscreen 110 or other method as specified above to finish pairing medication dispenser 100 and its serial number with the user account (if this option was used). The user would now be considered the "owner" of medication dispenser 100.

a. In the current embodiment, there will only be one owner per medication dispenser 100 to enhance security and responsibility per medication dispenser 100. Owner accounts could be moved from one medication dispenser 100 to another and one owner could own multiple medication dispenser 100s. In other embodiments, one medication dispenser 100 could have multiple owners.

7. The user and now "owner" of medication dispenser 100 will be given access to the user interface that allows medication dispenser 100 to be setup, including times medications are taken, what medications are taken, and what notifications are associated with particular times medications are taken and other events (FIG. 1).

8. The owner would have the option of adding subscribers (described below) to their medication dispenser 100 by entering the relevant information to identify a unique subscriber account, such as an associated subscriber account email.

a. In the current embodiment, the owner would maintain control of who was allowed to be a subscriber to medication dispenser 100 they own and could remove a subscriber at any point through a user interface or other means.

b. The owner could maintain control of the number of features and data that are available to each subscriber. For example, one subscriber may be able to access the medications a subscriber is taking, whereas another could only access the times medications were taken.

Subscriber Account Setup and Use:

In a similar manner, subscriber accounts must be setup. The "subscriber" account could be set up through a web or app interface that would contain standard account registration fields such as a name, email, and password. If the user intends to setup and use a medication dispenser 100 (as specified above), they could be given the option to complete an "owner" account rather than an "subscriber" account. More specifically, setup would involve a subscriber being required to specify if they are a covered entity by HIPAA, such as someone who is associated with a hospital or home health care organization. Once completed, the user would be considered a "subscriber" and have control of a "subscriber account".

A "subscriber" account would have the option to request access to specific features and data of "owner" accounts and medication. One method to request access would be to have a user interface that allows a subscriber to type in the email or other unique identifier of an "owner" account. After requesting access to an "owner" account associated with a medication dispenser 100, a notification could be sent to the "owner" account, through email or other means (e.g. a notification on medication dispenser 100). The "owner" account would then have to approve whether they would like to give access to the particular subscriber account that is requesting access.

If the "subscriber" account confirms it is a covered entity under HIPAA, the "owner" account could be required to waive HIPAA protection for their PHI through an online form or other means for that particular "subscriber." The step could be bypassed if the "subscriber" was not a covered entity. This distinction allows the company selling medication dispenser 100 to maintain HIPAA compliance with a variety of users. For example, a family member who is not considered a covered entity would not require the owner of medication dispenser 100 to sign a HIPAA waiver whereas a nursing director for a home health care organization would require the owner of a medication dispenser 100 to sign a HIPAA waiver. In addition, if the company is HIPAA compliant, these steps could be removed. This could also be given as a warning rather than waiver. The owner account could also choose to de-identify the information associated with their medication dispenser 100 (*s*) so that the information sent to the subscriber would no longer be PHI as it is not associated with an identifier.

Following these guidelines, the "owner" could then confirm that the subscriber could have access to the account through a number of methods such as clicking on a custom URL on a web page (the owner could also have control over which exact type and amount information being sent, with de-identification as specified above, or only access to specific parts or data such as medications and times dispensed). Once subscribed to an "owner's" account (after their approval) and hence a particular medication dispenser 100 or medication dispenser 100s, the subscriber could have access to a limited number of features and/or data as specified by the owner or defaulted by the company. One such piece of access would simply be an API with the stream of that user's adherence data. In the current embodiment, certain parts of the user interface that an "owner" account would have access to are limited for the "subscriber" account.

Figure 7:
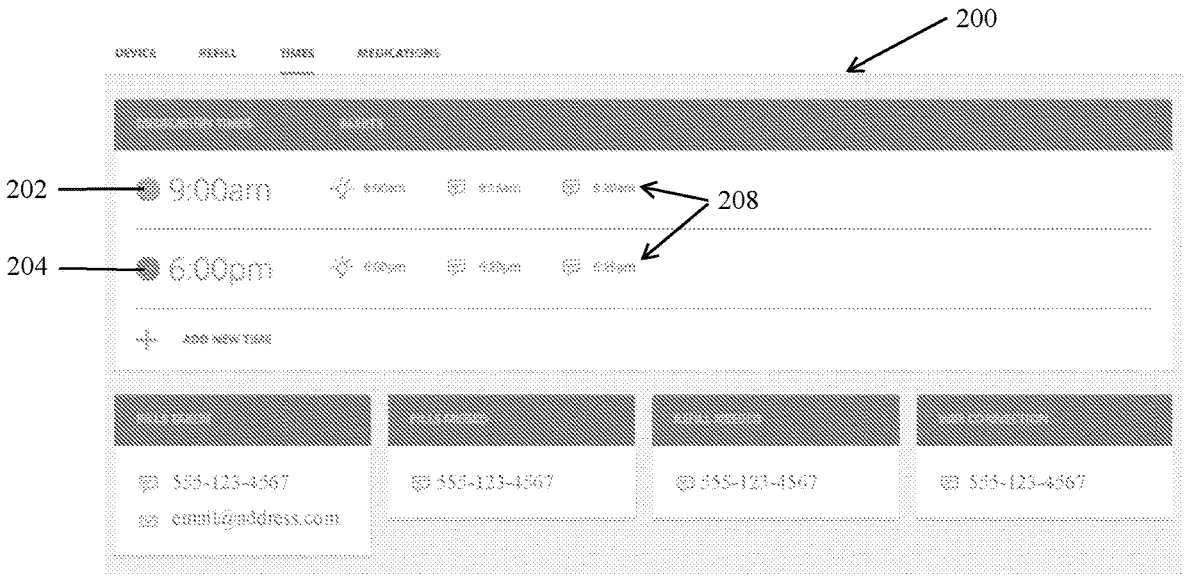
FIG. 7 illustrates one example of an Owner Account User Interface.

Referring to FIG. 7, an example of an "Owner" account user interface 200 with full access to all features that is present with the owner account. As presented here, the user is able to set up the times a medication will be taken throughout the day. The dots 202 and 204 (which can be colored using any number colors) associated with specific times are used to simplify the association between the times of day dispensing occurs, the compartments dispensed at each time, and the medication in each compartment. As illustrated, there are two times that medication dispenser 100 will dispense in this example so there are two dots. If there were more or less dispensing times, then there would also be the same number of associated dots (or other indicators). Associated with each time of dispensing is a number of reminders 208. In this example, each time of dispensing (9:00 am and 6:00 pm) is associated with three reminders, a light and two text reminders. In an "owner" account, a user would be able to see the reminders that were implemented by the user as well as any reminders that were placed by subscriber accounts. In the current embodiment, there can only be one sound or light reminder associated with each event, because it is a binary event (ON/OFF) that occurs only on medication dispenser 100 (unlike a text or email message which occurs remotely). Because of this, the "owner" account would be the only account that would have access to light and sound reminders. Unlike light and sound reminders, there can be any number of text, email, and phone reminders and a subscriber could have the ability to place their own (and remove them).

The owner account would also have the ability to place and remove their own reminders, but also the ability to remove "subscriber" reminders. Below the "MEDICATION TIMES" tab are a number of tabs representing specific events ("PILLS TAKEN", "PILLS MISSED", "REFILL NEEDED", "WIFI CONNECTION". Under each event, is a number of notifications associated with each event. These notifications are either text, email, or phone reminders for each event in the current embodiment. There can be any number of events rather than the four displayed, such as "LID 102 OPENED" or "TRAY MOVED". Similar to reminders above, each event can have text or email notifications trigger when the event happens (rather than at a specific time as above).

An owner account would have the ability to place notifications and the ability to remove "subscriber" notifications. A subscriber could have the ability to place (and remove) their own notifications for each event, but would not have the ability to change the owners or other subscribers events (same as with reminders above).

Figure 8:
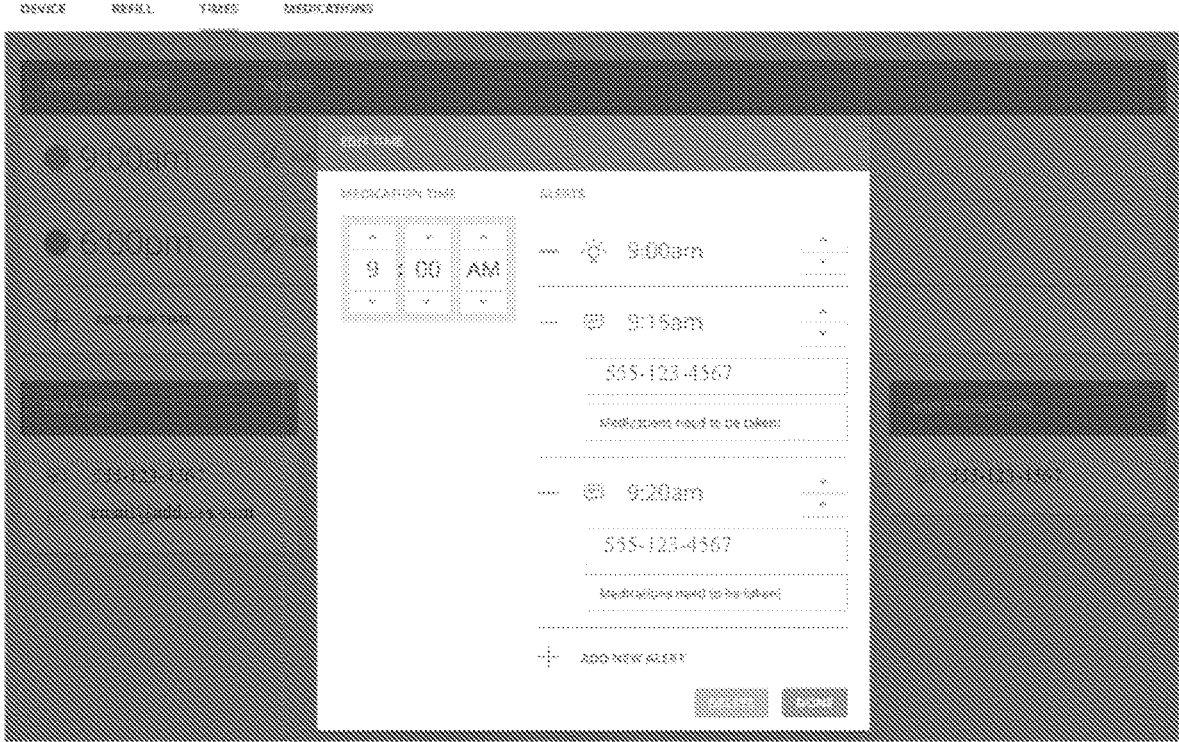
FIG. 8 is a subsection of the user interface as shown in FIG. 7, with a modal popup used to edit a specific dispense time (9:00 AM) of that day.
Figure 9:
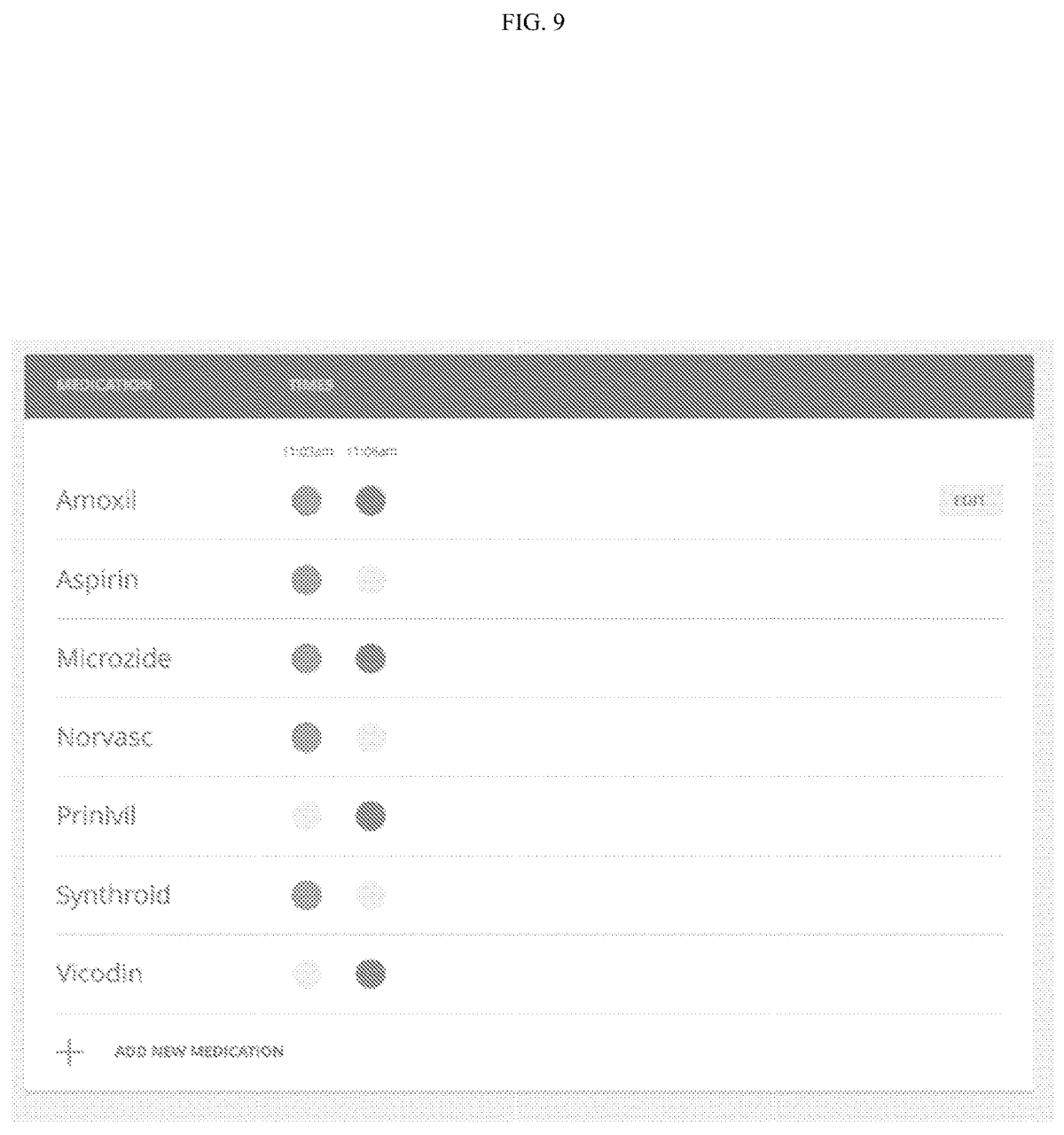

In the owner account, the user would have full access and be able to change the timing of dispenses (e.g. from 9 am to 10 am). An owner account would also be able to add/remove reminders and remove subscribers reminders, as illustrated in FIG. 8. In the current embodiment, as best illustrated in FIG. 9, the "owner" account is able to have access to the "EDIT" button and the "ADD NEW MEDICATION". Dispense times in this example are 11:03 and 11:06 am rather than the 9 am and 6 pm in the above examples. Each of the dots 202 and 204 are associated with a specific dispense times for each of the medications. For example, Amoxil is taken at both dispense times as potentially represented by the fulfilled colored dots (i.e. could be green and orange color dots, for example). Further, Aspirin is only taken at 11:03 am with the fulfilled first dot (green) but not the second dot (orange).

Figure 10:
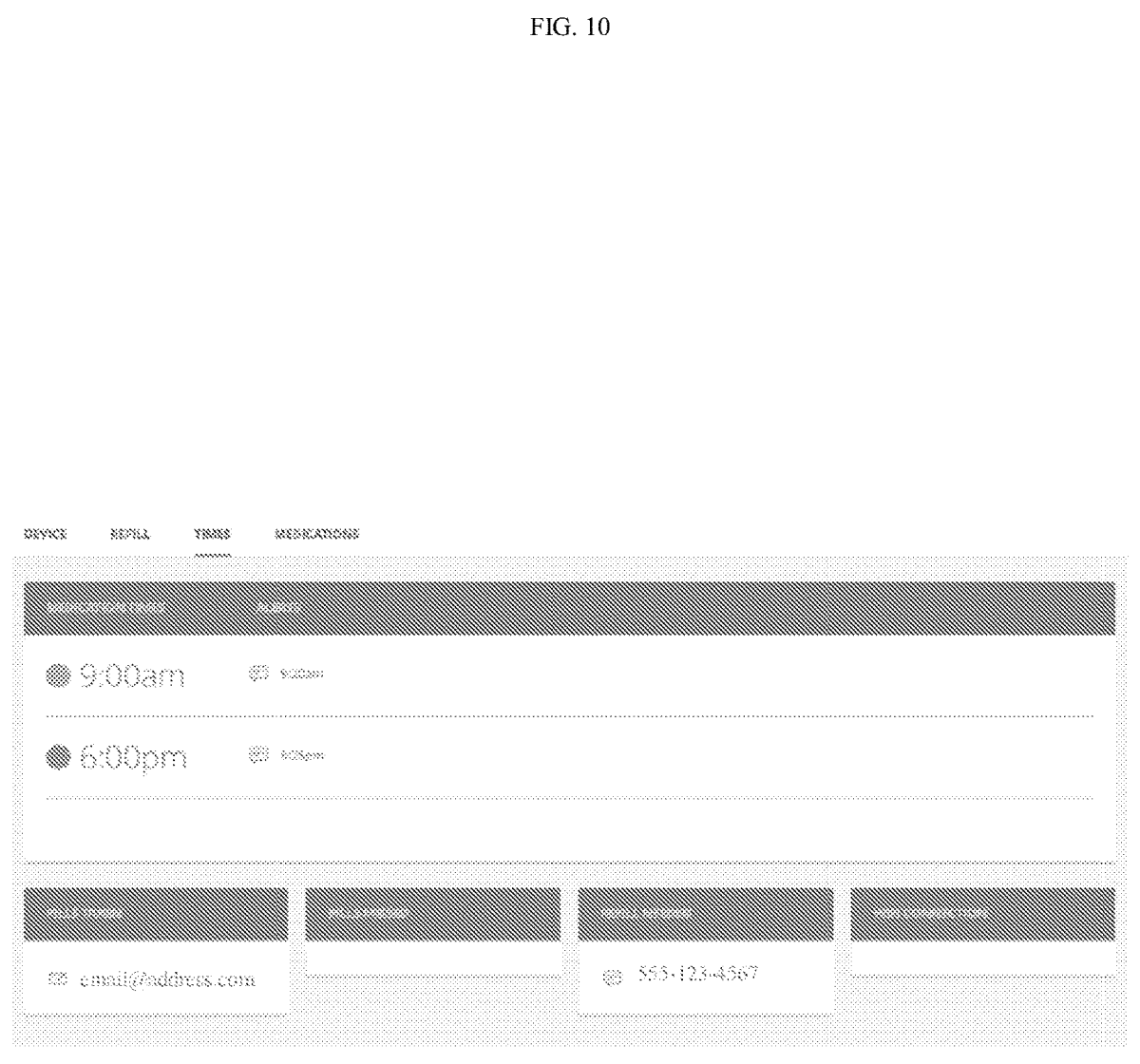

FIG. 10 further shows a corresponding user interface to set up the times a medication will be taken throughout the day for a "subscriber" account vs. the "owner" account in FIG. 7. Here, only the "subscriber" account is shown, allowing the subscriber to see and edit the reminders (a text message at 9:20 am and at 6:25 pm) that the particular subscriber has added. In this embodiment, the "subscriber" account cannot see or edit the reminders that are set by an "owner" account or other "subscriber" accounts. In other embodiments, this restriction could be removed. Similarly, the "subscriber" account in this example can only see and edit the notifications it has placed (an email for a "PILLS TAKEN" event and a text for a "REFILL NEEDED" event).

Figure 11:
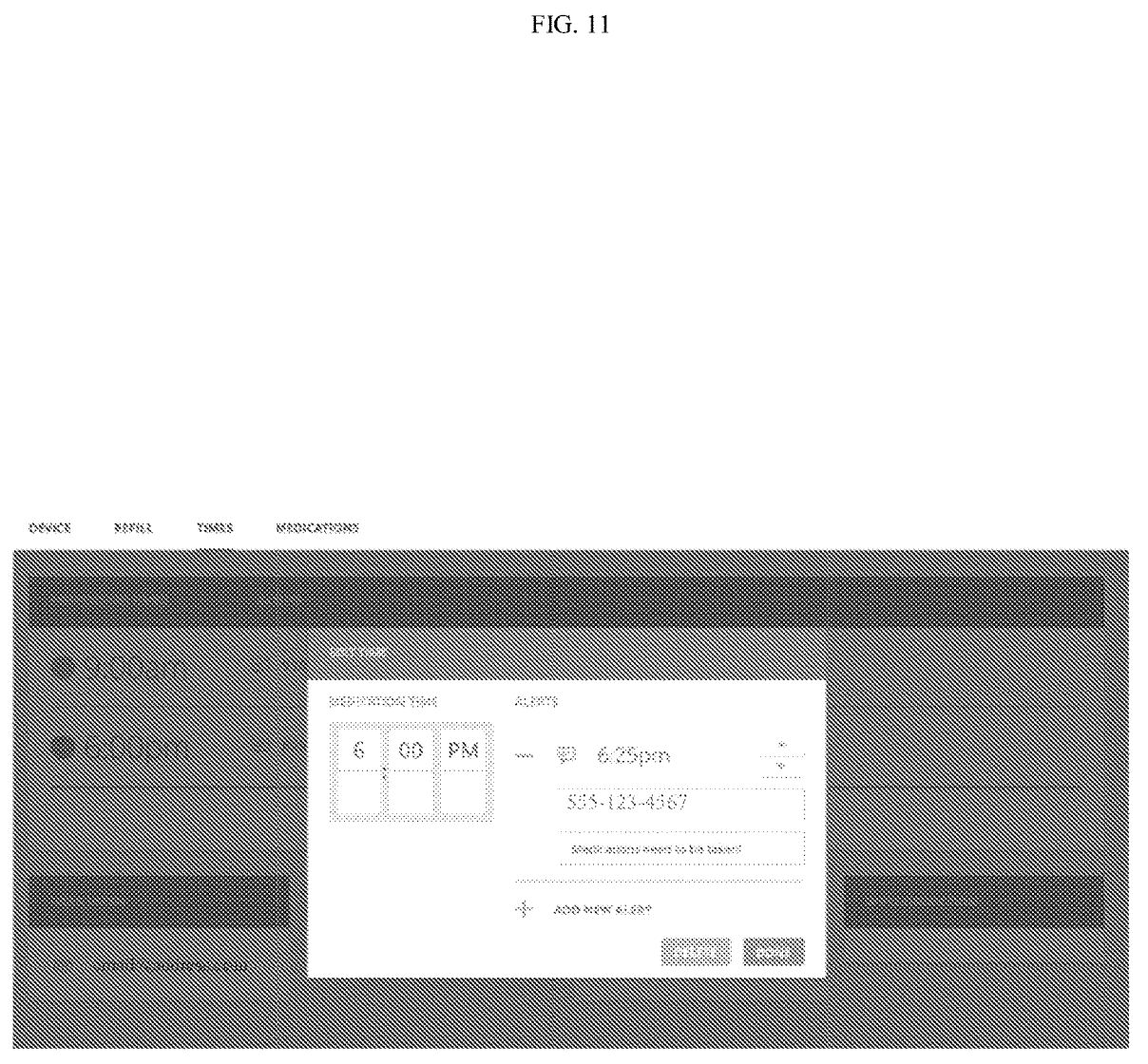

A modal popup is used to edit a specific dispense time (9:00 AM) of that day, as shown in FIG. 11. Unlike FIG. 8 for the "owner" account, here the "subscriber" account is unable to change the "MEDICATION TIME" from 6:00 PM to other times. Limiting "subscriber" accounts in this way prevent more than one party (i.e. anyone other than the "owner") from changing a crucial setting on medication dispenser 100. The "subscriber" account is still able to alter the text reminder and its associated settings for the reminder that they set. In this example, (as shown in FIG. 11) the "subscriber" account is not able to access other reminders set by the "owner" account or other "subscriber" accounts.

In the current embodiment, the "subscriber" account is not able to have access the "EDIT" button and the "ADD NEW MEDICATION" that are present for and "owner" account in FIG. 9. By preventing one or multiple "subscriber" accounts from being able to alter the medication schedule of the pill-taker, one can assure that only the "owner" account is able to make changes.

Figure 13:
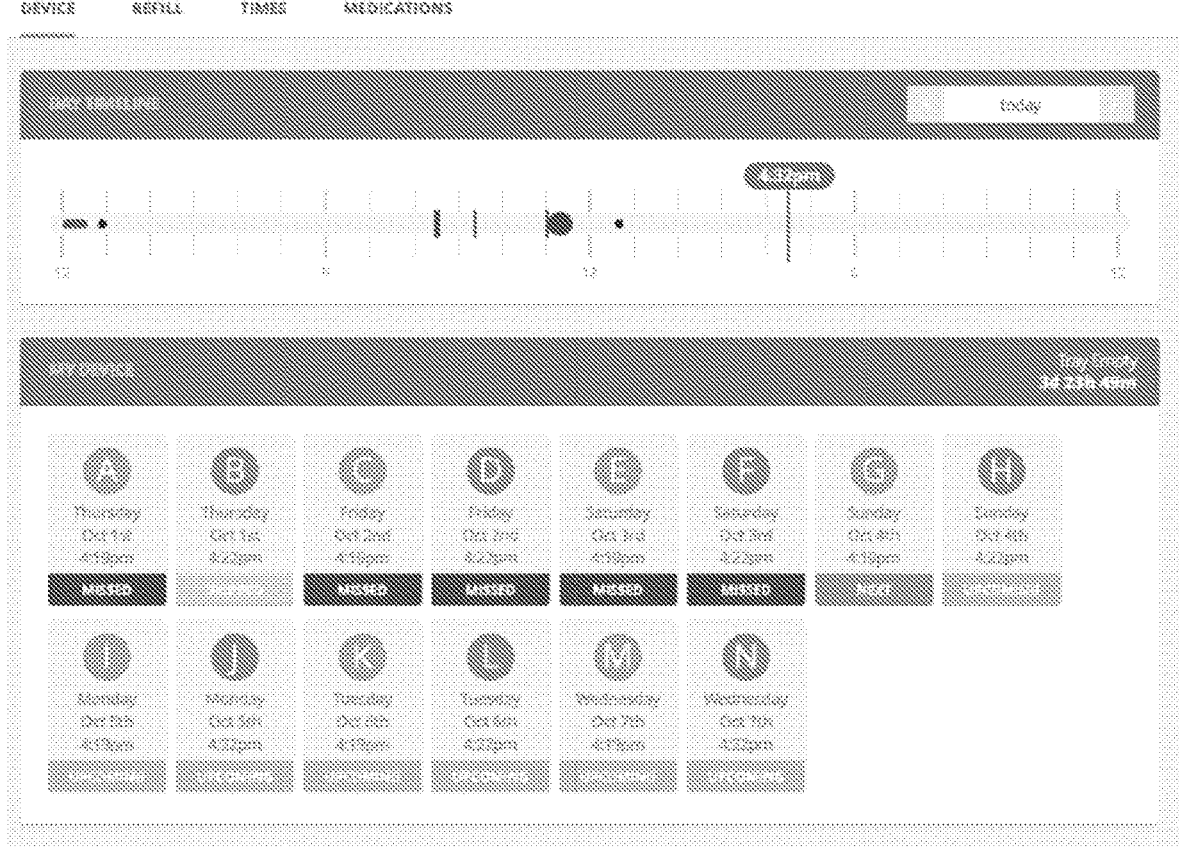
FIG. 13 shows a dashboard view of a medication dispenser.
Figure 14:
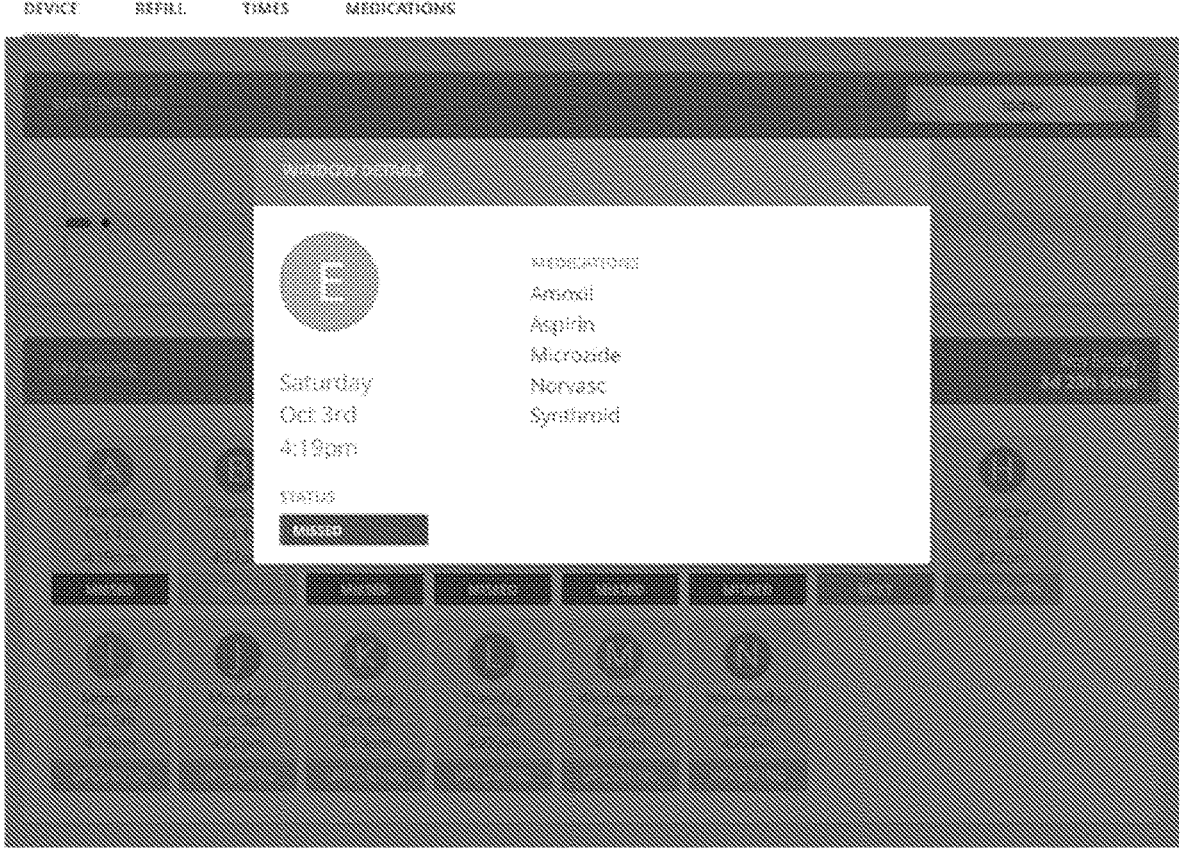
FIG. 14 presents a more detailed popup based upon the dashboard of FIG. 13.

Turning now to FIGS. 13 and 14, a dashboard view of medication dispenser 100 is illustrated. Here, each of the compartments are presented with a labelled letter (i.e. letters A-M). In addition, each of the compartments also has an associated status indicator, such as MISSED, SKIPPED, NEXT, or UPCOMING to indicate what is the history or next upcoming action related to the particular compartment. In addition, there is also a day timeline to indicate the windows of time when medication are available, and other significant events, such as disconnecting, updates, refills, and other events. The timeline could also back in time to see other days along with their associated events.

Cassette Specific Features:

To facilitate swapping and identification of the removable cassettes into medication dispenser 100 of the current embodiment, specific labelling methods, electronic or otherwise, could be used. For example, an RFID tag could be embedded into a cassette with a reader within the electronics of medication dispenser 100. If the RFID tag did not match the expected cassette when read by medication dispenser 100, any number of actions could occur, including sending text notifications, storing the information on a remote server, flashing or alarming at medication dispenser 100, and prevention of operation. Similarly, if the RFID tag did match the expected cassette when read by medication dispenser 100 medication dispenser 100 could continue to function normally (as well as sending a number of medications) or any number of events could occur including sending text notifications and storing the information on a remote server. Rather than using a RFID tag or other electronic means such as NFC or low energy bluetooth, a physical marking could be present on medication dispenser 100 such as a number of notches or other physical markings could be used. A bar coding system could also be used. Reading each of these different marking systems could be accomplished with different reading systems such as physical switches or a barcode reader.

A cassette may also come pair with a sealable top in order to preserve medications contained within the compartment. A membrane may be used between the lid 102 and cassette to keep the lid 102 airtight to further airtight.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A medication dispensing system comprising:
    a cassette having a plurality of compartments, with each compartment being configured to contain a plurality of medications;
    a housing containing the cassette and accommodating controlled access to the plurality of compartments;
    a lid comprising an aperture providing selective access to the cassette and the plurality of compartments, wherein the cassette includes the plurality of compartments and an area without compartments, the area without compartments being arrangeable to block the aperture and restrict access to the plurality of compartments;
    a drive mechanism coupled to the housing and the lid to control movement of the cassette relative to the housing;
    an accelerometer positioned within the housing or the lid and configured to detect an orientation of the medication dispensing system; and
    a control system configured to engage the drive mechanism only when the accelerometer detects a desired orientation to allow the controlled access to the plurality of compartments based upon a dispensing schedule having a plurality of dispensing events stored in the control system.

2. The medication dispensing system of claim 1, further comprising a security interface coupled to a user interface, the security interface configured to disable the user interface and the control system in a first state, the security interface configured to allow access to the user interface in a second state.

3. The medication dispensing system of claim 2, wherein the second state is accessed after receiving an acceptable passcode input to the security interface.

4. The medication dispensing system of claim 2, wherein the security interface includes an array of buttons.

5. The medication dispensing system of claim 2, wherein the security interface includes an array of electronic sensors.

6. The medication dispensing system of claim 2, wherein the security interface and user interface are coupled to a memory, the memory configured to record operating data relating to the security interface and the user interface.

7. The medication dispensing system of claim 1, further comprising an identification module configured to provide a set of identification data relating to each of the plurality of compartments.

8. The medication dispensing system of claim 7, wherein the housing comprises an identification reader, and the identification module is arranged to be read by the identification reader when received by the housing.

9. The medication dispensing system of claim 8, wherein the identification module comprises a radio frequency identification (RFID) tag and the identification reader comprises an RFID interrogator.

10. The medication dispensing system of claim 1, wherein the cassette further comprises an engagement feature configured to engage with the drive mechanism.

11. The medication dispensing system of claim 1, wherein the cassette is circular.

12. The medication dispensing system of claim 1, wherein a plurality of medications are dispensed from the plurality of compartments through the aperture.

13. The medication dispensing system of claim 1, further comprising a display screen.

14. The medication dispensing system of claim 13, wherein the display screen is a touchscreen.

15. The medication dispensing system of claim 13, wherein the display screen is configured to provide an indicator for each of the plurality of compartments indicative of medications to be positioned within each of the plurality of compartments.

16. The medication dispensing system of claim 1, wherein the cassette comprises an inner ring and an outer ring, and wherein each compartment of the plurality of compartments is defined by opposed sidewalls extending between the inner ring and the outer ring.

17. The medication dispensing system of claim 16, wherein each of the sidewalls defines a slot adjacent to the inner ring, the slot configured to maintain a label providing an identifier for each compartment of the plurality of compartments.

18. The medication dispensing system of claim 1, wherein the cassette includes a notch configured to interface with the drive mechanism.

* * * * *